(12) United States Patent
Levin

(10) Patent No.: US 11,034,924 B2
(45) Date of Patent: Jun. 15, 2021

(54) PHOTOBIOREACTOR

(71) Applicant: Alexander Levin, Binyamina (IL)

(72) Inventor: Alexander Levin, Binyamina (IL)

( * ) Notice: Subject to any disclaimer, the term of this patent is extended or adjusted under 35 U.S.C. 154(b) by 313 days.

(21) Appl. No.: 16/040,566

(22) Filed: Jul. 20, 2018

(65) Prior Publication Data

US 2020/0024558 A1 Jan. 23, 2020

(51) Int. Cl.
*C12M 1/00* (2006.01)
*C12M 3/00* (2006.01)
*C12M 1/12* (2006.01)
*C12N 1/20* (2006.01)
*C12N 1/12* (2006.01)

(52) U.S. Cl.
CPC ............ *C12M 1/002* (2013.01); *C12M 23/06* (2013.01); *C12M 23/22* (2013.01); *C12M 29/12* (2013.01); *C12M 29/14* (2013.01); *C12N 1/12* (2013.01); *C12N 1/20* (2013.01)

(58) Field of Classification Search
USPC ......... 435/292.1, 289.1, 294.1, 305.1; 47/1.4
See application file for complete search history.

(56) References Cited

U.S. PATENT DOCUMENTS

| | | | | |
|---|---|---|---|---|
| 3,468,057 A * | 9/1969 | Buisson | ................ | A01G 33/00 435/257.1 |
| 3,955,317 A * | 5/1976 | Gudin | ................... | C12M 21/02 435/420 |
| 3,998,186 A * | 12/1976 | Hodges | ................... | A01K 61/59 119/207 |
| 4,084,346 A * | 4/1978 | Stengel | ................... | C12M 23/18 435/292.1 |
| 5,443,985 A * | 8/1995 | Lu | ......................... | C12M 23/50 435/296.1 |
| 5,534,417 A * | 7/1996 | Arad | ...................... | A01G 33/00 435/257.1 |
| 5,741,702 A * | 4/1998 | Lorenz | .................. | B01D 53/84 435/292.1 |
| 5,846,816 A * | 12/1998 | Forth | .................... | C12M 29/14 435/292.1 |
| 5,981,271 A * | 11/1999 | Doucha | ................. | A01G 33/00 435/292.1 |
| 6,827,036 B2 * | 12/2004 | Connolly | ............... | A01K 63/04 119/208 |
| 8,110,395 B2 * | 2/2012 | Lewnard | ................. | C12N 1/12 435/292.1 |
| 8,245,440 B2 * | 8/2012 | Ryan | ..................... | C12M 21/02 47/62 C |
| 8,318,478 B2 * | 11/2012 | Dahle | ................... | C12M 21/02 435/292.1 |
| 8,361,786 B2 * | 1/2013 | Hu | ........................ | C12M 23/44 435/292.1 |

(Continued)

*Primary Examiner* — Nina Bhat

(57) ABSTRACT

A photobioreactor with a microalgae's cultivation chamber in the form of a duct that is constructed from an inflatable sleeve from transparent polymer film; this inflatable sleeve excluding its terminal sections is sandwiched between a bank of frames with wire nettings from below and glass panes from above the inflatable sleeve, and it has a small inclination regarding the horizontal plane. The terminal sections of the inflatable sleeve are in fluid communication with two headers, which are used for supplying and removal of gaseous medium and suspension of microalgae into and out of the duct.

14 Claims, 9 Drawing Sheets

(56) References Cited

U.S. PATENT DOCUMENTS

| | | | |
|---|---|---|---|
| 8,986,985 B2 * | 3/2015 | Levin | C12M 23/20 |
| | | | 435/292.1 |
| 9,938,492 B2 * | 4/2018 | Gressel | A01G 22/00 |
| 2007/0155006 A1 * | 7/2007 | Levin | C12M 23/04 |
| | | | 435/292.1 |
| 2009/0011492 A1 * | 1/2009 | Berzin | B01D 53/84 |
| | | | 435/257.1 |
| 2009/0130706 A1 * | 5/2009 | Berzin | C12M 21/02 |
| | | | 435/41 |
| 2010/0028976 A1 * | 2/2010 | Hu | C12M 41/12 |
| | | | 435/257.1 |
| 2011/0258920 A1 * | 10/2011 | Licamele | C12M 23/02 |
| | | | 47/1.4 |
| 2011/0300624 A1 * | 12/2011 | Tian Kian Wee | C12M 23/04 |
| | | | 435/292.1 |
| 2014/0242681 A1 * | 8/2014 | Fiorentino | C12N 1/12 |
| | | | 435/287.1 |
| 2016/0130546 A1 * | 5/2016 | Leimbach | C12M 23/38 |
| | | | 435/257.1 |

\* cited by examiner

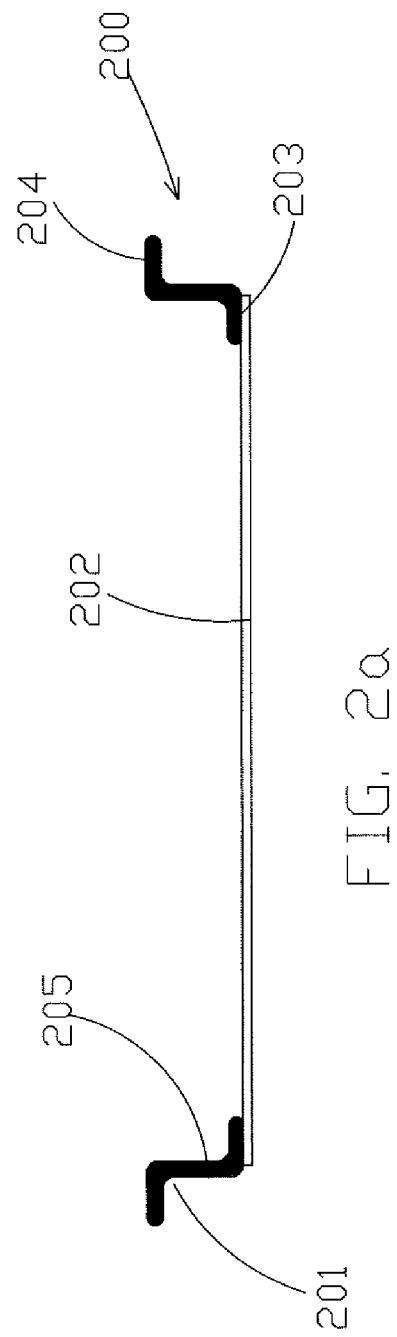

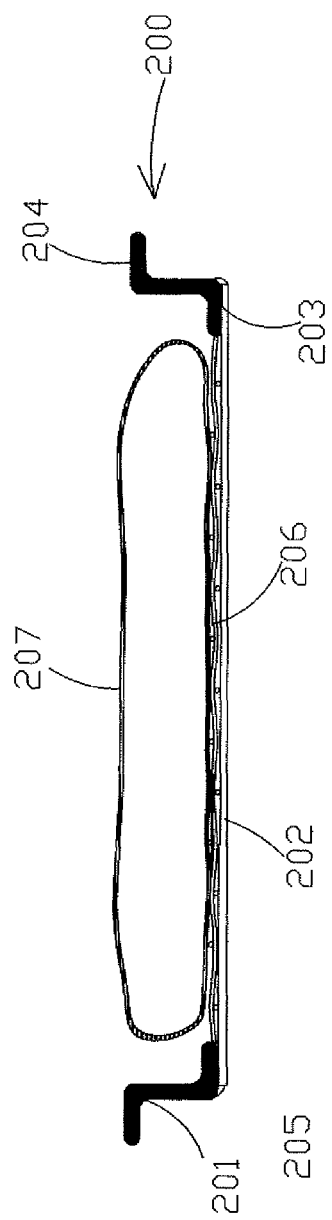

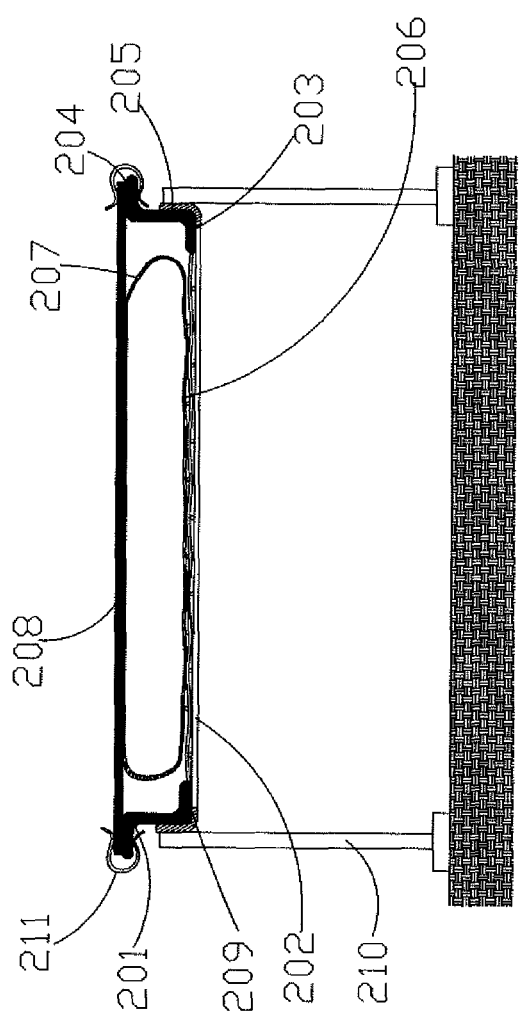

PHOTOBIOREACTOR

BACKGROUND OF THE INVENTION

This invention relates to the field of bioreactors for cultivation of microalgae or cyanobacteria.

Mass cultivation of microalgae or cyanobacteria has a great potential for modern agriculture, biochemistry and pharmaceutics.

Algal species: *Spirulina, Dunaliella* and others present important sources of vitamins, proteins, unsaturated fats, organic compounds of iron and other microelements. The most common forms of microalgae or cyanobacteria cultivation photobioreactors are open ponds or open raceways channels.

There are some technical problems connected with application of such systems:

a) Light distribution within photobioreactors constructed as ponds or channels presents a serious problem. The depth of the pond or raceway channels should be in the range of 15/30 cm.

It determines in turn relatively low final microalgae (or cyanobacteria) concentration in nutritious solution and high cost of harvesting microalgae biomass.

b) Mixing the nutritious solution in order to prevent cell sinking, and, in addition, to remove from the nutritious solution the generated oxygen, which inhibits photosynthesis process.

c) It is necessary to provide an adequate amount of $CO_2$, which is required for performance of photosynthesis process; this $CO_2$ is supplied as a rule from the ambient air or from gaseous medium enriched with $CO_2$ by its dissolution in the nutritious solution.

d) Maintenance of optimum ranges of daily and nightly temperatures of the nutritious solutions.

There are patents and patent applications, which are devoted to solve a part of the above-mentioned problems; however, these patents and patent applications do not provide sufficiently effective and cheap solutions of the described problems.

U.S. Pat. No. 4,084,346 describes a system of channels intended for algae growing; there are discharge means installed in these channels which introduce $CO_2$, into the microalgae suspension.

U.S. Pat. No. 3,468,057 describes a basin for culture of algae in an aqueous nutrient medium comprising, in combination, at least two illuminated horizontal zones, at least two inclined zones and at least one gas injection means.

U.S. Pat. No. 3,955,317 describes a method for growing plant cells containing chloroplasts in liquid suspension simultaneously with the growth of photosynthetic bacteria, in which method the liquid suspension containing the plant cells is enclosed in a first elongated, at least partially transparent, container and a liquid suspension of photosynthetic bacteria is contained in second elongated, at least partially transparent, container, the said second container being attached to the said first container so that light passing through the said first container then passes through the said second container; the said containers preventing passage of liquid from one container to the other, the containers being supported on a body of water; the liquid suspension in the first container being exposed to light and brought into contact with carbon dioxide.

U.S. Pat. No. 3,998,186 describes a method and apparatus for shrimp culture; shrimp hatched and brought through larval and post-larval stages environment unit which includes plastic cover means positioned over an elongated waterway containing seawater, or the like, and algae in substantial amounts. The design of the unit and the technique of intermittently supplying seawater allows the control of light intensity and light spectral characteristics within the shrimp growing area and the control of seawater flow rate, temperature and dissolved oxygen content of the seawater in the waterway.

U.S. Pat. No. 5,443,985 describes a bioreactor for culturing living cells, particularly shear sensitive cells, wherein the bioreactor is composed of a stationary vessel with opposite spaced walls inclined at an angle to form upper and lower walls. Liquid culture medium and cell culture, such as hybridoma cells, are introduced into the vessel and gas is introduced at the lower end of the vessel to form gas bubbles which travel upward along the upper wall of the bioreactor to disengage from a small portion of the gas liquid interface. The gas bubbles circulate the cells and liquid medium, maintaining the cells in suspension and lifting them in a circulating path upwardly parallel to the upper wall and downward along the lower wall. The bioreactor design thus achieves bulk mixing and aeration by maintaining a significant degree of segregation between the upwardly travelling bubbles and the cells in the liquid medium avoiding unnecessary cell damage by fluid-mechanical shear or by bubble bursting events.

U.S. Pat. No. 5,534,417 describes a method of growing microalgae, which uses the outdoor sunlight as a source of energy. Growth is confined to an assembly of vertical, transparent tubes through which nutrient and air is carried with carbon dioxide. The microalgae is periodically harvested from the tubes.

U.S. Pat. No. 5,741,702 describes a reactor vessel for processing gases containing carbon dioxide by means of a fluid containing algae; this reactor vessel comprises: a first elongated duct having a rectangular cross section with a top surface and a bottom surface for containing said gases and said fluid containing algae; a second elongated duct, abutting said first elongated duct, having a rectangular cross section with a top surface and a bottom surface, said duct having ribs extending from said bottom surface to said top surface to form a plurality of elongated channels for insulating said first elongated duct; wherein the channels of said second elongated duct are constructed so as to be evacuated to create a vacuum therein.

U.S. Pat. No. 5,846,816 describes a bioreactor for biomass production comprising: a substantially transparent chamber, the chamber being at least suitable for containing biomass in a liquid phase, and having a base portion, an upper portion and a number of side walls between the base portion and the upper portion, the side walls being configured so as to generally diverge from the base portion towards the wider upper portion; and circulating means for circulating the contents of the chamber, wherein the circulating means creates a motive force within the liquid phase sufficient to ensure continual mixing of substantially all of the biomass and at least cyclical exposure of biomass to a light source.

U.S. Pat. No. 5,981,271 describes process of outdoor thin-layer cultivation of algae in which suspension of algae saturated with carbon dioxide and enriched with necessary nutrients, is distributed on inclined cultivation areas where the suspension of algae is distributed on inclined cultivation areas under turbulent flow which depends on velocity of flow, on coefficient of roughness of the cultivation surfaces, on the thickness of the algal suspension layer and on inclination of the cultivation surface. Between individual cultivation areas carbon dioxide is supplied into the suspension and the suspension flowing from the lowest cultivation area is conveyed into the collecting tank from which it is pumped on the upper edge of the highest cultivation area. Bioreactor for accomplishing the mentioned process is composed of at least two individual cultivation meandering areas where the lower end of the upper area and the beginning of the next lower area, inclined in the opposite direction, are connected by channels in which outlets for supply of carbon dioxide into suspension are placed.

U.S. Pat. No. 8,110,395 describes a photobioreactor system comprising: a plurality of interconnectable photobioreactor sections which, when connected together, form at least one longitudinally-oriented photobioreactor unit of the photobioreactor system, the photobioreactor sections each comprising a liquid flow channel, and a light-transparent cover that forms a gas headspace between the cover and the liquid flow channel, the cover being constructed and arranged to cover at least a substantial portion of the liquid flow channel and configured to provide the gas headspace even when a gas pressure within the photobioreactor unit is less than the atmospheric pressure surrounding the photobioreactor section, at least one photobioreactor unit of the photobioreactor system further including an evaporative cooling area, including a reservoir and a sprayer, the evaporative cooling area being disposed outside of the cover such that the reservoir is open to the atmosphere outside of the cover, the reservoir being in fluid communication with the liquid flow channel, the sprayer is configured to spray a liquid upwardly from within the reservoir.

U.S. Pat. No. 6,827,036 describes aquaculture apparatus comprising an elongate tube of flexible translucent material, the tube extending longitudinally along a tube site and having a lower section defining a water course, and a cover extending externally over the tube and being air supported, said cover being at least partially spaced from the tube and providing an insulating space for insulating at least a substantial part of the tube.

U.S. Patent Application No. 20090130706 describes an enclosed photobioreactor configured to float on a body of water; the photobioreactor comprises: an elongated, longitudinally-oriented photobioreactor section constructed and arranged to contain a liquid medium comprising phototrophic organisms therein, the photobioreactor section comprises: a substantially flexible lower barrier comprising an upper surface in contact with and supporting the liquid medium; a cover constructed and arranged to cover the liquid medium within the photobioreactor section and further constructed and arranged to provide a gas headspace under the cover and above the liquid medium, the cover being at least partially transparent to light of a wavelength capable of driving photosynthesis; a first floatation element disposed on a first lateral side of the photobioreactor section; a second floatation element disposed on a second lateral side of the photobioreactor section; the first and second floatation elements being constructed and arranged to support the photobioreactor section for floatation on the body of water; and a plurality of tensioners constructed and arranged to apply tension to the lower barrier so as to maintain a substantial portion of the area of the lower barrier in a substantially horizontal configuration when the photobioreactor section is charged with the liquid medium, such that a continuous layer of the liquid medium has a substantially uniform depth which extends from approximately the first floatation element to approximately the second floatation element over at least a portion of the area of the lower barrier.

U.S. Patent Application No. 20100028976 describes a photobioreactor comprising: (a) a container adapted for holding fluid, comprising (i) opposing first and second sidewalls, wherein at least one of the first and second sidewalls is transparent; (ii) opposing first and second endwalls; (iii) a container bottom; and (iv) a container cover, wherein the first and second sidewalls comprise a plurality of separate sections, and wherein the separate sections are in fluid communication; (b) support struts for connecting the plurality of separate sections of the first and second sidewalls; (c) at least one inlet port in fluid communication with the container; (d) at least one outlet port in fluid communication with the container; (e) an aeration system in fluid communication with the container; and (f) a temperature control system connected to the container so as to control temperature of fluid within the container.

It should be noted that these US Patents and Patent Applications (including U.S. Pat. No. 5,981,271) do not solve construction problems of an elongated photobioreactor with length of some tens of meters to some hundreds of meters and with small inclination regarding the horizontal plane, wherein such photobioreactor is provided with effective means for enhancement of heat and mass transfer between the liquid and gaseous mediums in it.

U.S. Pat. No. 9,938,492 describes a photobioreactor for cultivating and growing microalgae comprising: (i) a sealed thin, visible light conducting flexible plastic sheeting comprising an upper plastic sheeting panel and a lower plastic sheeting panel, the upper plastic sheeting panel and the lower plastic sheeting panel collectively forming a sealed tubular flat container, whereby one face of the lower plastic sheeting panel floats on the surface of a temperature modulating body of water and wherein the other face of the lower plastic sheeting panel is coated with microalgae within an aqueous medium forming a thin aqueous microalgae layer that is less than 1 cm in thickness; and where said upper plastic sheeting panel is held above the thin aqueous microalgae layer due to the slightly inflated airspace.

An attempt to solve these problems is presented in U.S. Pat. No. 8,986,985 to the author of this invention.

Reviews of technical problems connected with design of industrial photobioreactors are presented in the articles: James C. Ogbonna, Hideo Tanaka "Industrial-size photobioreactors" CHEMTECH 1997, 27(7), 43-49. and O. Pulz "PHOTOBIOREACTORS: PRODUCTION SYSTEM FOR PHOTOTROPHIC MICROORGANISMS" Springer-Verlag, 2001.

This invention proposes further modifications of the technical solutions described in U.S. Pat. No. 8,986,985. This modification makes the photobioreactor simpler in its construction, cheaper and more reliable.

SUMMARY OF THE INVENTION

A photobioreactor of this invention is constructed from several main elements.

There are two parallel posts' rows and two parallel rows of inclined supporting angles, which are installed on these posts. These posts and supporting angles form a supporting structure with the preset inclination angle, preferably, in the range of 0.1 degree/2. degree.

This supporting structure includes as well a bank of frames with fastened in them wire nettings: the frames are mutually abutted and are positioned in-line with the small inclination to the horizontal plane.

In another version, each frame may be provided with a set of parallel rods instead of the wire netting.

Each frame is fabricated from two longitudinal Z-profiles and two transverse strips. It is possible to apply other profiles with upper horizontal shelves instead of Z-profiles: angles, C-channels, U-channels, I-beams.

There is a wire netting installed in each frame excluding the terminally positioned frames, which are provided with rigid sheets.

In another version the wire netting can be substituted by a bank of parallel rods installed on the bottom shelves of the Z-profiles or on the transverse strips of the frame.

In an additional version the wire nettings are substituted by glass panes installed in the frames.

A sleeve from transparent flexible polymer is situated on the frames and is supported by the frames' wire nettings. Each terminal section of the sleeve is provided with a port. These ports are formed in the sleeve by welding owing the rigid sheets of the terminally positioned frames.

There are bank of glass panes, which are mutually abutted and positioned in-line on the upper shelves of the Z-profiles of the frames (excluding the terminally positioned frames) and fastened on the upper shelves by fasteners, for example, by spring clips. The glass panes are fabricated preferably from UV blocking glass.

These glass panes play several functions: protection of the polymer sleeve against destruction by UV component of solar radiation and from hail. In addition, the glass panes allow easier cleaning their upper surfaces of the photobioreactor from dust.

In addition, the glass panes in combination with the frames' wire nettings form a substantially flat duct in the polymer sleeve intended for flow of thin layer of microalgae suspension (broth) and gaseous medium with $CO_2$ component.

The glass panes can be substituted by transparent (or translucent) polymer sheets.

It should be noted that for substantially long closed photobioreactors their average operation pressure of gaseous medium can significantly exceed the hydraulic pressure of thin layer of microalgae suspension.

This causes a cylindrical-wise inflated shape of the polymer sleeve and. therefore, a segment-wise shape of the thin layer of microalgae suspension flowing on the bottom of the polymer sleeve. Application of the glass panes prevents this phenomenon.

As it was noted, the terminal sections of the polymer sleeve are provided with inlet and outlet ports in the case of gas-liquid co-current flow in the flat closed duct, or with inlet-outlet ports in the case of gas-liquid counter flow in the flat duct.

The angles of inclination of the supporting structure can very along the flat duct.

In particular, these angles of inclination may be of relatively small values for the proximal sections of the flat duct (regarding flow direction of the microalgae suspension) with gradually increasing the inclination angles at the middle and distal sections of the flat duct. It allows choosing an optimal change of the microalgae suspension depth along the whole length of the flat duct.

The inlet and outlet ports are in fluid communication with two headers, which serve for supply of the air or gaseous medium enriched with $CO_2$ into the internal space of the flat duct and removal of the air or the gaseous medium from this internal space. In addition, these ports serve for supply of suspension of microalgae or cyanobacteria into the internal space of the flat duct and withdrawal of suspension of microalgae or cyanobacteria from this internal space.

The header, which serves for supply of the microalgae suspension into the flat duct can be provided with a level gauge ensuring control of an optimal flow rate of the microalgae suspension.

Air or gaseous medium with $CO_2$ supplied into the proximal header (regarding flow direction of the gaseous medium) can be previously cooled and/or dried; it allows establishing optimal temperature of the microalgae suspension along the flat duct.

It should be noted, that the elongated flexible polymer sleeve, which forms the flat duct, is functioning as a flexible elastic membrane. Such flexible membrane vibrates in response to the gaseous medium flow with enhancement of heat and mass transfer between the gaseous medium and the thin layer of microalgae suspension.

Application of this effect in heat exchangers is described in the article: Yanhua Lu et al. ENHANCED PERFORMANCE OF HEAT RECOVERY BY AIR-INDUCED FILM VIBRATION, International Journal of Thermal Science, 49, July 2010 pp. 2037/2041.

This effect can be enhanced by variable pressure in the internal space of the flat duct, when this pressure variation is executed with a specific frequency.

The elongated flexible polymer sleeve is fabricated from transparent or translucent polymer film. This allows utilizing as well solar radiation reflected from below onto the flat duct.

There is another method of setting off vibration of the bottom cover of the flat duct.

This effect can be obtained by application of intermittent air jets, which are arrive onto the underside of the flat duct from a flat zigzag pipe (or flat zigzag pipes) with a set of perforations oriented toward the bottom of this flat duct; pressurized air with pulsating pressure is supplied into the flat zigzag pipe.

The supporting angles can be provided with aligning screws in order to minimize misalignment of the frames with the wire nettings (or of the terminal frames provided with the rigid sheets) and to achieve even distribution of the microalgae suspension across the width of the flat duct.

BRIEF DESCRIPTION OF THE DRAWINGS

FIG. 2*a* and FIG. 2*b* show elevation and cross-section views of a frame with Z-profiles used for construction of the longitudinal sides of the frame.

FIG. 2*c* shows a cross-section of the frame with the wire netting and un-inflated polymer sleeve situated on the wire netting.

FIG. 2*d* shows a cross-section of the inflated flat duct of the photobioreactor, which is fastened on posts.

DESCRIPTION OF PREFERABLE EMBODIMENTS

Figure 1:
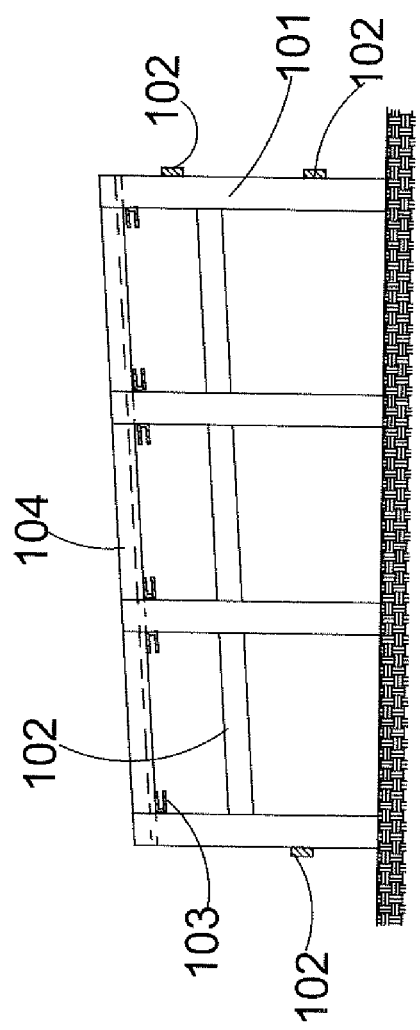
FIG. 1 demonstrates the Prior Art of a side view of supporting angles installed on posts.

FIG. 1 demonstrates a side view of supporting angles installed on posts. It comprises: posts 101 with cross-bars 102; a supporting angle 103 and transverse channel bars 104.

Figure 2B:
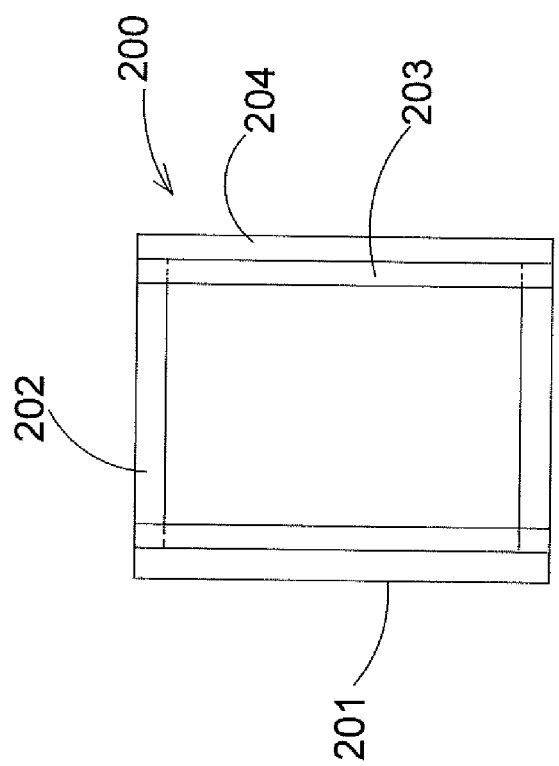

FIG. 2a and FIG. 2b show elevation and cross-section views of frame 200 with Z-profiles, which are used for construction of the longitudinal sides of frame 200.

Frame 200 comprises Z-profiles 201 and transverse cross-bars 202.

Each Z-profile comprises a bottom shelf 203, an upper shelf 204 and a middle section 205.

FIG. 2c shows a cross-section of frame 200 with an installed wire netting. It comprises: Z-profiles 201, transverse cross-bars 202, the wire netting 206 and a non-inflated polymer sleeve 207 situated on the wire netting 206.

FIG. 2d shows a cross-section of the inflated flat duct of the photobioreactor, which is fastened on posts.

It comprises: Z-profiles 201 (with their upper shelves 204, middle sections 205 and bottom shelves 203), the transverse cross-bars 202, the wire netting 206, the inflated polymer sleeve 207, a glass pane 208, supporting angles 209, posts 210 and fasteners 211.

Figure 3:
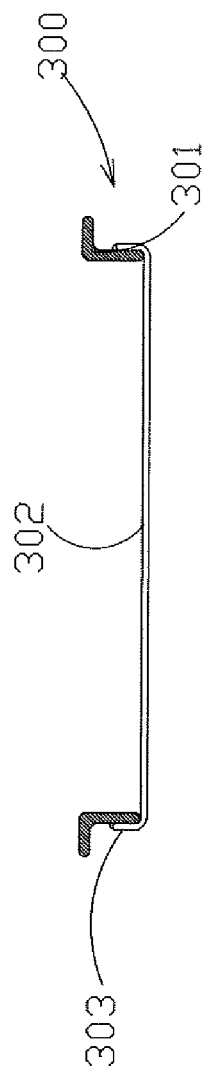
FIG. 3 shows a cross-section of a frame with application of angle profiles for construction of the longitudinal sides of the frame.

FIG. 3 shows a cross-section of frame 300 with application of angle profiles for construction of the longitudinal sides of frame 300.

It comprises longitudinal angle profiles 301, which is bonded with strips 302 with bowed terminal sections 303.

Figure 4:
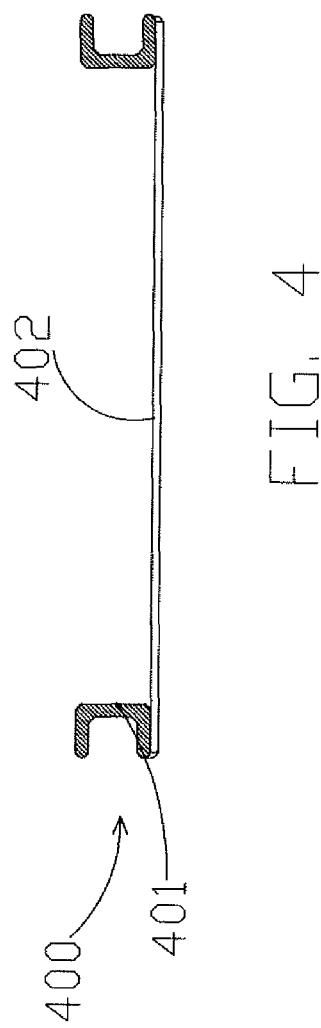
FIG. 4 shows a cross-section of a frame with application of U-profiles for construction of the longitudinal sides of the frame.

FIG. 4 shows a cross-section of frame 400 with application of U-profiles for construction of the longitudinal sides of frame 400. It comprises longitudinal U-profiles 401, which is bonded with strips 402.

Figure 5:
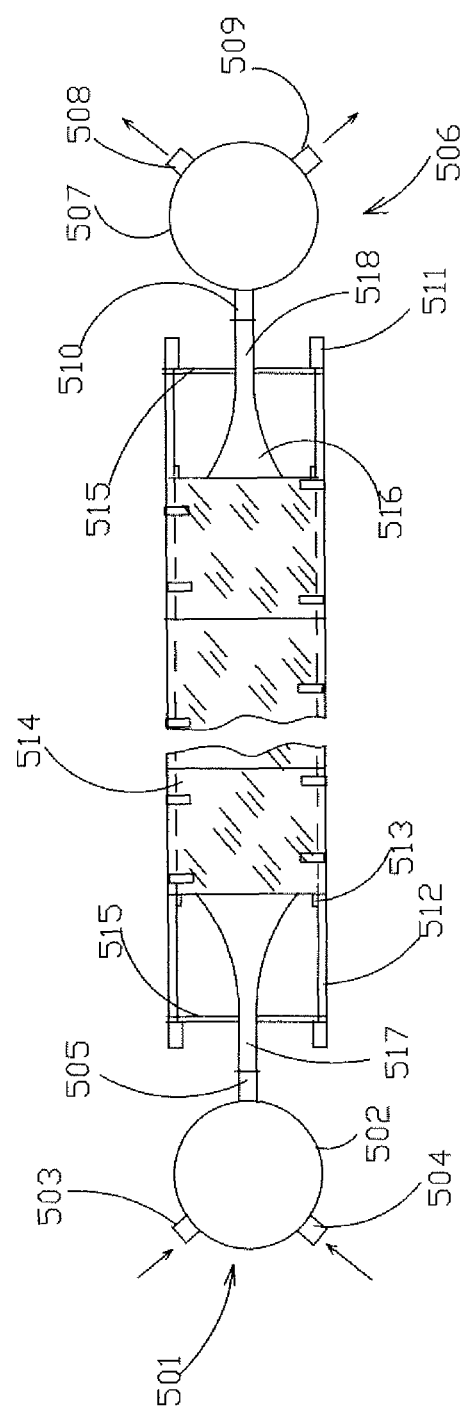
FIG. 5 shows the Prior Art of an elevation view of the photobioreactor including two headers.

FIG. 5 shows an elevation view of a photobioreactor including two headers.

It comprises: header 501 with housing 502, an gas inlet connection 503, a broth (microalgae suspension) inlet connection 504, a gas-broth outlet port 505; header 506 with housing 507, an gas outlet connection 508, a broth outlet connection 509, an inlet gas-broth port 510; posts 511; supporting angles 512; Z-profiles 513 of non-terminal frames; glass panes 514; terminal frames 515; a polymer sleeve 516 with an inlet and outlet ports 517 and 518.

Figure 6:
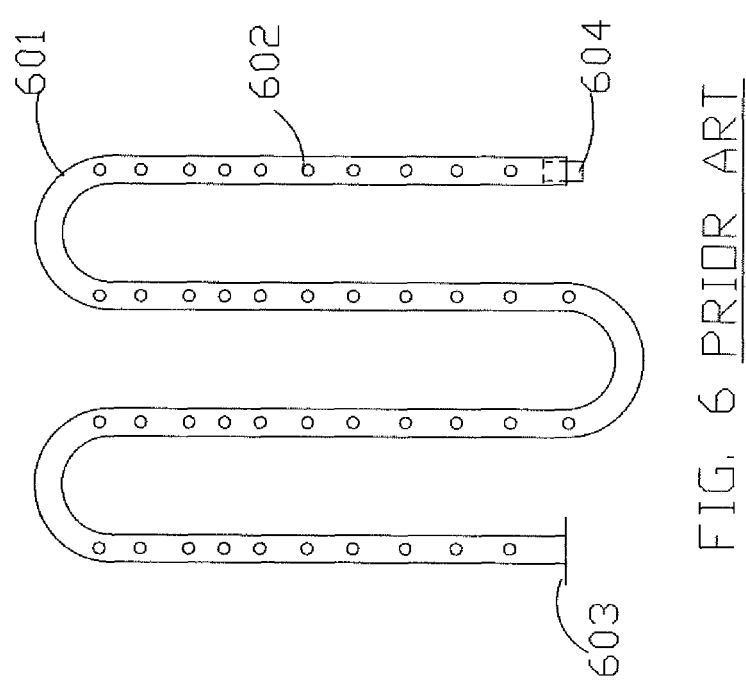
FIG. 6 demonstrates the Prior Art of a top view of a flat zigzag pipe to be installed below the frames with the wire nettings.

FIG. 6 shows a flat zigzag pipe, which is provided with a set of openings; one end of this flat zigzag pipe is plugged and the other end is provided with an inlet connection. It comprises: the flat zigzag pipe 601; openings 602; the inlet connection 603 and plug 604.

The invention claimed is:

1. A photobioreactor for cultivation of microalgae or cyanobacteria comprising a support structure comprising a plurality of posts, a plurality of cross bars and a plurality of supporting angles wherein said plurality of cross bars and said plurality of supporting angles installed on said posts constructed and arranged to provide a bank of frames fastened with wire nettings;

said bank of frames further comprising an inflatable transparent or translucent film polymeric sleeve sandwiched between a bank of abutted in-line line frames with wire nettings disposed on an underside of said polymeric sleeve;

wherein each frame of said bank of frames includes two longitudinal Z-profiles and two transverse strips and wherein said bank of frames includes transparent or translucent glass panes in connection with lateral sections of said frame;

wherein said inflatable polymeric sleeve an includes inlet port and an outlet port and when said polymeric sleeve when inflated forms a small duct and is inclined at an angle determined by the incline of the abutted frames;

wherein said Z-profiled frame section supports said transparent or translucent glass panes and include fastening members to secure said glass panes; and wherein said support structure include two parallel row rows of posts and two parallel rows of inclined supporting angles secured to said posts;

and wherein said inflated polymeric sleeve duct is in operative connection with a first and a second external header including said inlet port and said outlet port for supplying and removing culturing media, aqueous suspension and/or gases into an out of the photobioreactor for culturing microalgae or cyanobacteria.

2. The photobioreactor as claimed in claim 1, wherein said header further includes a level gauge and a controller for monitoring the level of suspension within said photobioreactor.

3. The photobioreactor as claimed in claim 1, wherein said frames and supporting angles include aligning screws for preventing mis-alignment of said frames.

4. The photobioreactor as claimed in claim 1, wherein said glass panes is UV blocking glass.

5. The photobioreactor as claimed in claim 1, wherein said first header supplies microalgae suspension fluid into said inflated polymeric sleeve duct by a first inlet port and wherein the second header includes a second inlet port for supplying carbon dioxide into said shallow duct in counter-flow relationship with said first inlet port supply of microalgae suspension fluid.

6. The photobioreactor as claimed in claim 1, wherein said first header supplies microalgae suspension fluid into said inflated polymeric sleeve duct by a first inlet port and wherein the second header includes a second inlet port for supplying carbon dioxide into said shallow duct in co-current flow relationship with said first inlet port supply of microalgae suspension fluid.

7. The photobioreactor as claimed in claim 1, wherein the angles of inclination of said supporting angles gradually increases along the direction of flow in said shallow duct.

8. The photobioreactor as claimed in claim 1, wherein the frame is constructed with U-channels.

9. The photobioreactor as claimed in claim 1, wherein the frame is constructed with C-channels.

10. The photobioreactor as claimed in claim 1, wherein the frame is constructed with I-Beams.

11. The photobioreactor as claimed in claim 1, wherein the supply of carbon dioxide gas from said external header is applied with pulsating pressure to said shallow duct.

12. The photobioreactor as claimed in claim 1, wherein said inflatable sleeve is sandwiched between transparent or translucent polymeric sheets disposed above the frames and below the wire nettings are being below the frame.

13. The photobioreactor as claimed in claim 1, wherein said inflatable sleeve is sandwiched between UV filtering transparent or translucent polymeric sheets disposed above the frames and below the wire nettings are being below the frame.

14. The photobioreactor as claimed in claim 1, wherein said glass pans are fastened to said frames on the underside of said inflatable sleeve.

* * * * *